United States Patent
Inan

(10) Patent No.: US 10,921,307 B2
(45) Date of Patent: *Feb. 16, 2021

(54) DECONTAMINATING ROCK SAMPLES BY THERMOVAPORIZATION

(71) Applicant: Saudi Arabian Oil Company, Dhahran (SA)

(72) Inventor: Sedat Inan, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

This patent is subject to a terminal disclaimer.

(21) Appl. No.: 16/451,731

(22) Filed: Jun. 25, 2019

(65) Prior Publication Data

US 2019/0317070 A1    Oct. 17, 2019

Related U.S. Application Data

(63) Continuation of application No. 16/059,646, filed on Aug. 9, 2018, now Pat. No. 10,578,600.

(Continued)

(51) Int. Cl.
*G01N 33/24* (2006.01)
*G01N 1/44* (2006.01)
(Continued)

(52) U.S. Cl.
CPC .......... *G01N 33/241* (2013.01); *B09C 1/005* (2013.01); *B09C 1/065* (2013.01); *G01N 1/34* (2013.01);
(Continued)

(58) Field of Classification Search
CPC ..... B09B 3/0083; B08C 1/005; B08C 1/0065; G01N 1/34; G01N 1/44; G01N 25/00; G01N 33/241
See application file for complete search history.

(56) References Cited

U.S. PATENT DOCUMENTS

| 4,181,494 A | 1/1980 | Kimberley |
| 4,319,410 A | 3/1982 | Heilhecker et al. |

(Continued)

FOREIGN PATENT DOCUMENTS

| EP | 735928 | 10/1996 |
| EP | 915331 | 5/1999 |

(Continued)

OTHER PUBLICATIONS

International Search Report and Written Opinion issued in International Application No. PCT/US2018/046851 dated Dec. 4, 2018, 17 pages.

(Continued)

*Primary Examiner* — John Fitzgerald
(74) *Attorney, Agent, or Firm* — Fish & Richardson P.C.

(57) ABSTRACT

A rock sample includes multiple rock samples that are each obtained from the borehole. The rock samples have been exposed to contamination during a drilling operation to drill the borehole. The rock sample is split into a first sample portion and a second sample portion. The first sample portion is decontaminated with a solvent. The second sample portion is decontaminated by thermovaporization for an initial duration of time at an initial thermovaporization temperature below that of a cracking temperature of an organic matter carried within the rock sample. A difference between a first pyrolysis Tmax value of the first sample portion decontaminated by the solvent and a second pyrolysis Tmax value of the second sample portion decontaminated by the thermovaporization is determined to satisfy a decontamination level threshold. The remainder of rock samples are decontaminated by the thermovaporization in response to determining that the difference satisfies the decontamination level threshold.

10 Claims, 3 Drawing Sheets

Related U.S. Application Data

(60) Provisional application No. 62/546,753, filed on Aug. 17, 2017.

(51) Int. Cl.
| | |
|---|---|
| *B09C 1/06* | (2006.01) |
| *B09C 1/00* | (2006.01) |
| *G01N 1/34* | (2006.01) |
| *G01N 25/00* | (2006.01) |
| *B09B 3/00* | (2006.01) |

(52) U.S. Cl.
CPC ............... *G01N 1/44* (2013.01); *G01N 25/00* (2013.01); *B09B 3/0083* (2013.01)

(56) References Cited

U.S. PATENT DOCUMENTS

| | | | |
|---|---|---|---|
| 4,750,920 | A | 6/1988 | Manuel et al. |
| 5,294,061 | A | 3/1994 | Van Dijk |
| 5,390,529 | A | 2/1995 | Ghiselli |
| 5,843,787 | A | 12/1998 | Trabelsi et al. |
| 5,866,814 | A | 2/1999 | Jones et al. |
| 8,309,213 | B2 | 2/2012 | Clarke |
| 10,173,146 | B2 | 1/2019 | Bikass et al. |
| 10,578,600 | B2 * | 3/2020 | Inan ..................... G01N 25/00 |
| 2004/0144405 | A1 | 7/2004 | Garrick et al. |
| 2009/0211106 | A1 | 8/2009 | McKenzie |
| 2010/0304152 | A1 | 12/2010 | Clarke |
| 2012/0034428 | A1 | 2/2012 | Clarke |
| 2015/0135806 | A1 | 5/2015 | Hoff et al. |
| 2015/0346179 | A1 | 12/2015 | Pillot et al. |
| 2017/0095750 | A1 | 4/2017 | Bikass et al. |
| 2017/0175523 | A1 | 6/2017 | Abrams |
| 2019/0064039 | A1 | 2/2019 | Ammar et al. |

FOREIGN PATENT DOCUMENTS

| | | |
|---|---|---|
| EP | 2489505 | 8/2012 |
| GB | 2570023 A * | 10/2019 |
| JP | 61224994 | 10/1986 |
| WO | 2006003400 | 1/2006 |
| WO | 2009054995 | 4/2009 |
| WO | 2016186689 | 11/2016 |

OTHER PUBLICATIONS

Behar and Vandenbroucke, "Characterization and quantification of saturates trapped inside kerogen: Implications for pyrolysate composition," Organic Geochemistry, vol. 13, Issue 4-6, Jan. 1988.
Behar et al., "Rock-Eval 6 Technology: performance and developments," Oil and Gas Science and Technology, Rev. IFP, vol. 56, No. 2, Mar.-Apr. 2001, 25 pages.
Bernard et al., "Design and characterization of a thermochemical high-performance liquid chromatography flame photometric detector interface for the speciation of sulfur," The Analyst, Issue 7, 1994.
Carvajal-Ortiz and Gentzis, "Critical consideration when assessing hydrocarbon plays using Rock-Eval pyrolysis and organic petrology data: Data quality revisited," International Journal of Coal Geology, vol. 152, Part A, Nov. 1, 2015, 10 pages.
Christiansen et al., "Flash pyrolysis of coals, Temperature-dependent product distribution," Journal of Analytical and Applied Pyrolysis, vol. 32c, Apr. 1995, 13 pages.
Faure and Landais, "Rapid contamination screening of river sediments by flash pyrolysis-gas chromatography-mass spectrometry (PyGC-MS) and thermodesorption GC-MS (TdGC-MS)," Journal of Analytical and Applied Pyrolysis, vol. 57, No. 2, Feb. 2001, 16 pages.
Geel et al., "Palaeo-environment, diagenesis and characteristics of Permian black shales in the lower Karoo Supergroup flanking the Cape Fold Belt near Jansenville, Easter Cape, South Africa: Implications for the shale gas potential of the Karoo Basin," South African Journal of Geology, vol. 118, No. 3, Sep. 2015, 27 pages.
Geel et al., "Shale gas characteristics of Permian black shales in South Africa: Results from recent drilling in the Ecca Group (Eastern Cape)," Energy Procedia , vol. 40, Apr. 2013.
Han et al., "The Barnett Shale: Compositional fractionation associated with intraformational petroleum migration, retention, and expulsion," AAPG Bulletin, vol. 99, No. 12, Dec. 2015, 30 pages.
Hartwig and Schulz, "Applying classical shale gas evaluation concepts to Germany—Part 1: The basin and slope deposits of the Stassfurt Carbonate (Ca2, Zechstein, Upper Permian) in Brandenburg," Chemie der Erde—Geochemistry, vol. 70, Suppl. 3, Aug. 2010.
Horsfield et al., "Chapter 7: Microscale sealed vessel pyrolysis," in Grice, K. (Ed.), Principles and Practice of Analytical Techniques in Geosciences, Royal Society of Chemistry Detection Science Series 4, Sep. 11, 2014, 42 pages.
Iran et al., "Expulsion of oil from petroleum source rocks: Inferences from pyrolysis of samples of unconventional grain size," Organic Geochemistry, vol. 29, 1-3-3 part 1), Oct. 1998.
King, "Modified Method and Interpretation of Source Rock Pyrolysis for an Unconventional World," presented at the AAPG 2015 Annual Convention and Exhibition, May 31-Jun. 3, 2015, 4 pages.
Laggoun-Defarge et al., "Detection and characterization of natural oils in the microstructure of reservoir rocks by their fluorescence properties (detection et caraterisation des huiles naturelles dans la microstructure des roches reservoir par leurs proprietes de fluorescence)," Comptes Rendus—Academie des Sciences, Series II, vol. 314, No. 3, Jan. 1992, 6 pages.
Larter et al., "Reservoir Geochemistry: A link between Reservoir Geology and Engineering?" SPE Reservoir Engineering (Society of Petroleum Engineers) vol. 12, Issue 1, Feb. 1997, 6 pages.
Marshall, "Structural characterization of kerogen in 3.4 Ga Acheaen cherts from the Pilbara Craton, Western Australia," Precambrian Research vol. 155, 1-23, May 2007, 23 pages.
Monthioux and Landais, "Evidence of free but trapped hydrocarbons in coals," Fuel, vol. 66, No. 12, Dec. 1987.
Muscio et al., "Occurrence of thermogenic gas in the immature zone-implications from the Bakken in-source reservoir system," Organic Geochemistry, vol. 22, 3-5, Dec. 1994.
Ohya and Oguchi, "Utilization of membranes of H2O recycle system," SAE Technical Papers, Jan. 1985, 7 pages.
Romero-Sarmiento et al., "Artificial thermal maturation of source rocks at different thermal maturity levels: Application to the Triassic Montney and Doig formations in the Wester Canada Sedimentary Basin," Organic Geochemistry, vol. 97, Jul. 2016, 15 pages.
Romero-Sarmiento et al., "New Rock-Eval Method for Characterization of Unconventional Shale Resource Systems," Oil and Gas Science and Technology, Rev. IFP Energies nouvelles, vol. 71, No. 3, May-Jun. 2016, 9 pages.
Schaefer and Lythaeuser, "Low-molecular-weight hydrocarbons in sediments of Deep Sea Drilling Project Leg 89, Sites 585, East Mariana Basin and 586, Ontong-Java Plateau (Pacific)," Initial reports DSDP, Leg 89, 1986, 10 pages.
Schaefer et al., "Generation and migration of low-molecular-weight hyrdocarbons in sediments of deep sea drilling project Leg 79, site 544, 545, 547, offshore morocco," Initial Reports of the Deep Sea Drilling Project, 1984, 31 pages.
Schulz et al., "From shale oil to biogenic shale gas: retracing organic-inorganic interactions in the Alum Shale (furongian-lower Ordovician) in southern Sweden," AAPG Bulletin, vol. 99, No. 5, May 2015, 69 pages.
Shaefer and Lythaeuser, "Low-molecular-weight hydrocarbons in sediments of Deep Sea Drilling Project Leg 93, Hole 603B, off the East Coast of North America," Initial Reports, DSDP, Leg 93, 1987, 8 pages.
Tan et al., "Natural gas potential of Neoproterozic and lower Palaeozoic marine shales in the Upper Yangtze Platform, South China. Geological and organic geochemical characterization," International Geology Review, vol. 57, No. 3, Feb. 2015.
Wampler, "Book Review: Applied Pyrolysis Handbook," Feb. 8, 1995, 2 pages.

* cited by examiner

DECONTAMINATING ROCK SAMPLES BY THERMOVAPORIZATION

CROSS-REFERENCE TO RELATED APPLICATIONS

This application claims the benefit of priority to U.S. Utility application Ser. No. 16/059,646, filed Aug. 9, 2018 and entitled "DECONTAMINATING ROCK SAMPLES BY THERMOVAPORIZATION", which claims the benefit of priority to U.S. Provisional Patent Application Ser. No. 62/546,753, filed Aug. 17, 2017 and entitled "DECONTAMINATING ROCK SAMPLES BY THERMOVAPORIZATION," the contents of both of which are hereby incorporated by reference.

TECHNOLOGY FIELD

This disclosure relates to decontaminating rock samples.

BACKGROUND

Organic matter rich rocks are known to generate oil and/or gas upon maturation. In petroleum exploration, it is important to determine hydrocarbon generating potential of a given sedimentary rock intersected and sampled in exploration boreholes. Pyrolysis is routinely conducted as a screening analysis to estimate the maturity and remaining hydrocarbon generating potential of rock samples; these properties include total organic carbon content (TOC) and type of kerogen contained.

SUMMARY

This disclosure describes technologies relating to decontaminating rock samples by thermovaporization.

An example implementation of the subject matter described within this disclosure is a first method with the following features. A rock sample obtained from a borehole is decontaminate. The rock sample includes multiple rock samples that are each obtained from the borehole. The rock samples have been exposed to contamination during a drilling operation to drill the borehole. The rock sample is split into a first sample portion and a second sample portion. The first sample portion is decontaminated with a solvent. Decontaminating at least partially removes an organic contaminant from the first sample portion. The second sample portion is decontaminated by thermovaporization for an initial duration of time at an initial thermovaporization temperature below that of a cracking temperature of an organic matter carried within the rock sample. A difference between a first pyrolysis Tmax value of the first sample portion decontaminated by the solvent and a second pyrolysis Tmax value of the second sample portion decontaminated by the thermovaporization is determined to satisfy a decontamination level threshold. The remainder of rock samples are decontaminated by the thermovaporization in response to determining that the difference satisfies the decontamination level threshold.

Aspects of the example method, which can be combined with the example implementation alone or in combination, include the following. The thermovaporization includes heating up the second sample portion while passing an inert carrier gas over the second sample portion to at least partially decontaminate the second sample portion.

Aspects of the example method, which can be combined with the example implementation alone or in combination, include the following. Decontaminating the second sample portion includes elevating the initial thermovaporization temperature to greater than 350° C. for the initial duration.

Aspects of the example method, which can be combined with the example implementation alone or in combination, include the following. The initial duration is substantially 60 minutes.

Aspects of the example method, which can be combined with the example implementation alone or in combination, include the following. The initial thermovaporization temperature is elevated to substantially 375° C. and the initial duration is substantially 30 minutes.

Aspects of the example method, which can be combined with the example implementation alone or in combination, include the following. Determining the difference between a first decontamination level of the first sample portion by the solvent and a second decontamination level of the second sample portion by the thermovaporization includes determining that a difference between the maximum temperature of the first sample portion by the solvent and the maximum temperature of the second sample portion by the thermovaporization is less than 2° C.

Aspects of the example method, which can be combined with the example implementation alone or in combination, include the following. Decontaminating the remainder of the rock samples by the thermovaporization comprises simultaneously thermovaporizing the remainder of the plurality of rock samples within a single thermovaporization chamber.

Aspects of the example method, which can be combined with the example implementation alone or in combination, include the following. The rock samples include substantially seventy samples.

Aspects of the example method, which can be combined with the example implementation alone or in combination, include the following. The rock sample is a first rock sample. The rock samples include a second rock sample. The thermovaporization initial temperature or the initial duration of a thermovaporization process is adjusted based on determining that the difference does not satisfy the decontamination level threshold.

Aspects of the example method, which can be combined with the example implementation alone or in combination, include the following. Adjusting a duration of the thermovaporization process includes shortening a duration to be less than the initial duration by an amount of time sufficient to prevent the organic matter within the rock sample from cracking.

An example implementation of the subject matter described within this disclosure is a second method with the following features. A rock sample is thermovaporized to a thermovaporization temperature below that of a cracking temperature of organic matter carried within the rock sample. The thermovaporization temperature is sufficient to at least partially decontaminate the rock sample. Thermovaporizing the rock sample at the thermovaporization temperature is ceased.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Rock sample obtained from a geologic formation are often contaminated by excess organic material introduced to the borehole during the drilling process. Such organic molecules can come from diesel, oil-based drilling fluids, or any other organic fluid pumped into the borehole during drilling operations. These foreign organic molecules can contaminate rock sample from the geologic formation and can cause a systematic error when attempting to characterize the samples by geochemical analyses.

This disclosure describes a method for the removal of solvent soluble organic contaminants from a rock sample prior to subjecting the rock sample to pyrolysis analysis. The method includes placing a prepared rock sample into a pyrolysis chamber, heating up the rock sample while passing an inert carrier gas over the rock sample until contaminants are vaporized. The process is carried out at a low enough temperature and short enough duration to prevent kerogen maturation or cracking of the organic material.

Figure 1:
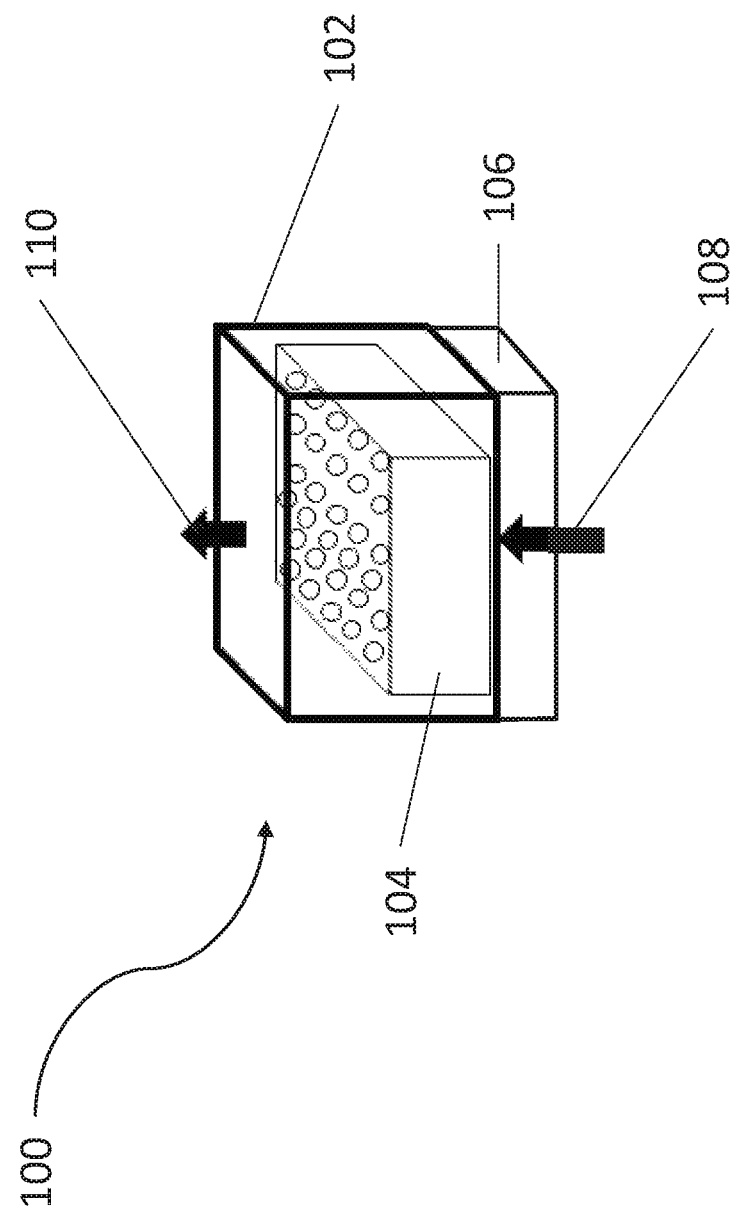
FIG. 1 is a perspective schematic diagram of a pyrolysis chamber.

FIG. 1 shows a schematic diagram of a pyrolysis system 100 that can be used to decontaminate a set of samples. The pyrolysis system 100 includes a pyrolysis chamber 102 in which a sample tray 104 can be placed. The pyrolysis chamber 102 and the sample tray can be of sufficient size to decontaminate several tens of samples in a single session, for example, seventy samples the pyrolysis chamber itself can be heated by a heating element 106. The heating element 106 can be an electric heating unit, a gas heating unit, or any other heating unit appropriate for heating the pyrolysis chamber to the desired temperature. The heating element 106 is capable of providing sufficient heat to heat the pyrolysis chamber 102 to a desired temperature for a pre-determined amount of time. The heating element 106 is also adjustable in the event that a desired temperature needs to be adjusted.

The pyrolysis chamber 102 has a gas inlet 108 and a gas outlet 110. During testing or decontamination, an inert gas, such as nitrogen, argon, or helium, flows into the pyrolysis chamber 102 through the gas inlet 108. The inert gas passes over the samples and carries away any volatile organic contaminants liberated due to a heat-induced decontamination process. The inert gas with the contaminant passes out of the pyrolysis chamber 102 through the gas outlet 110.

Figure 2A:
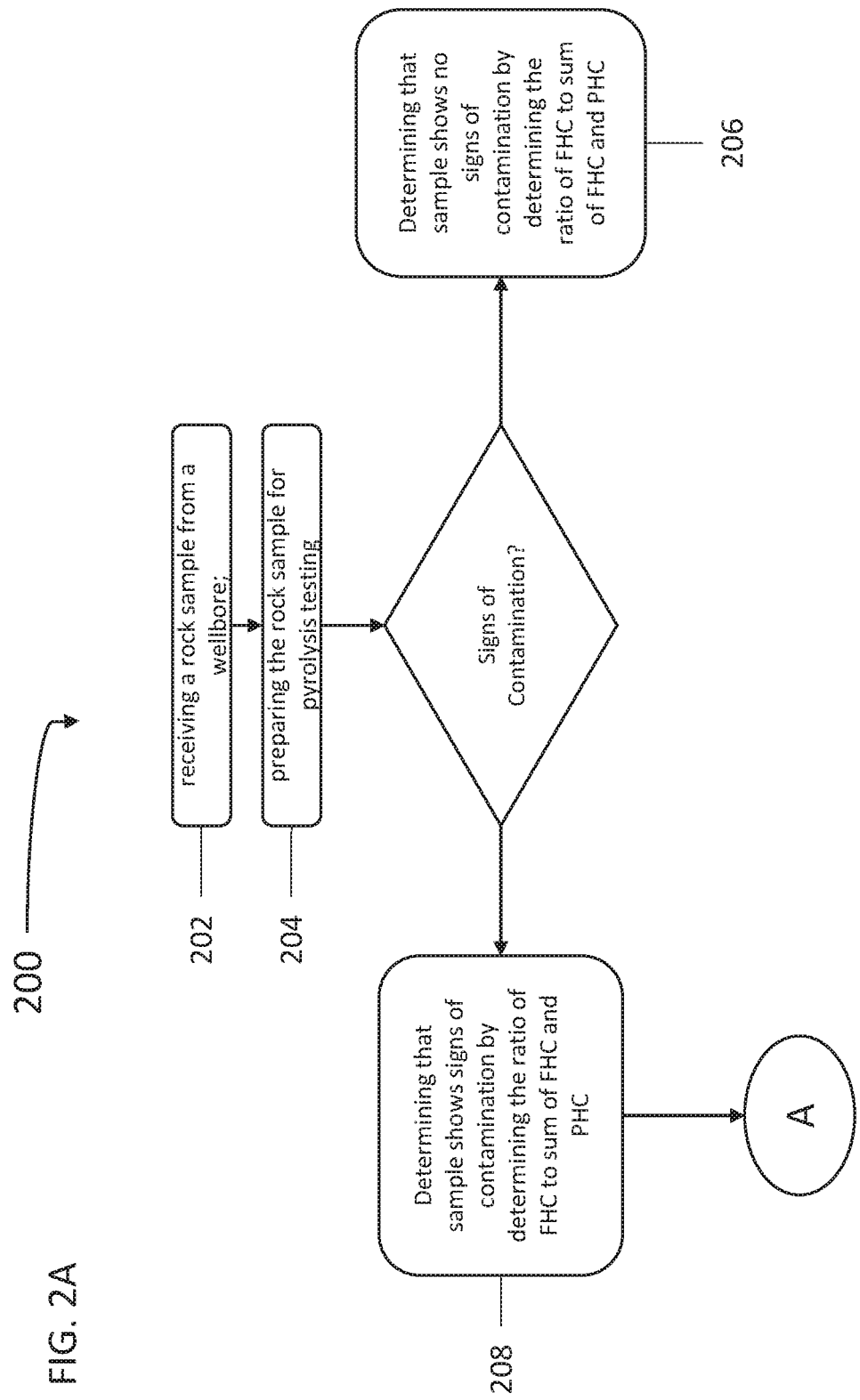
FIGS. 2A-2B is a flowchart of an example decontamination method.
Figure 2B:
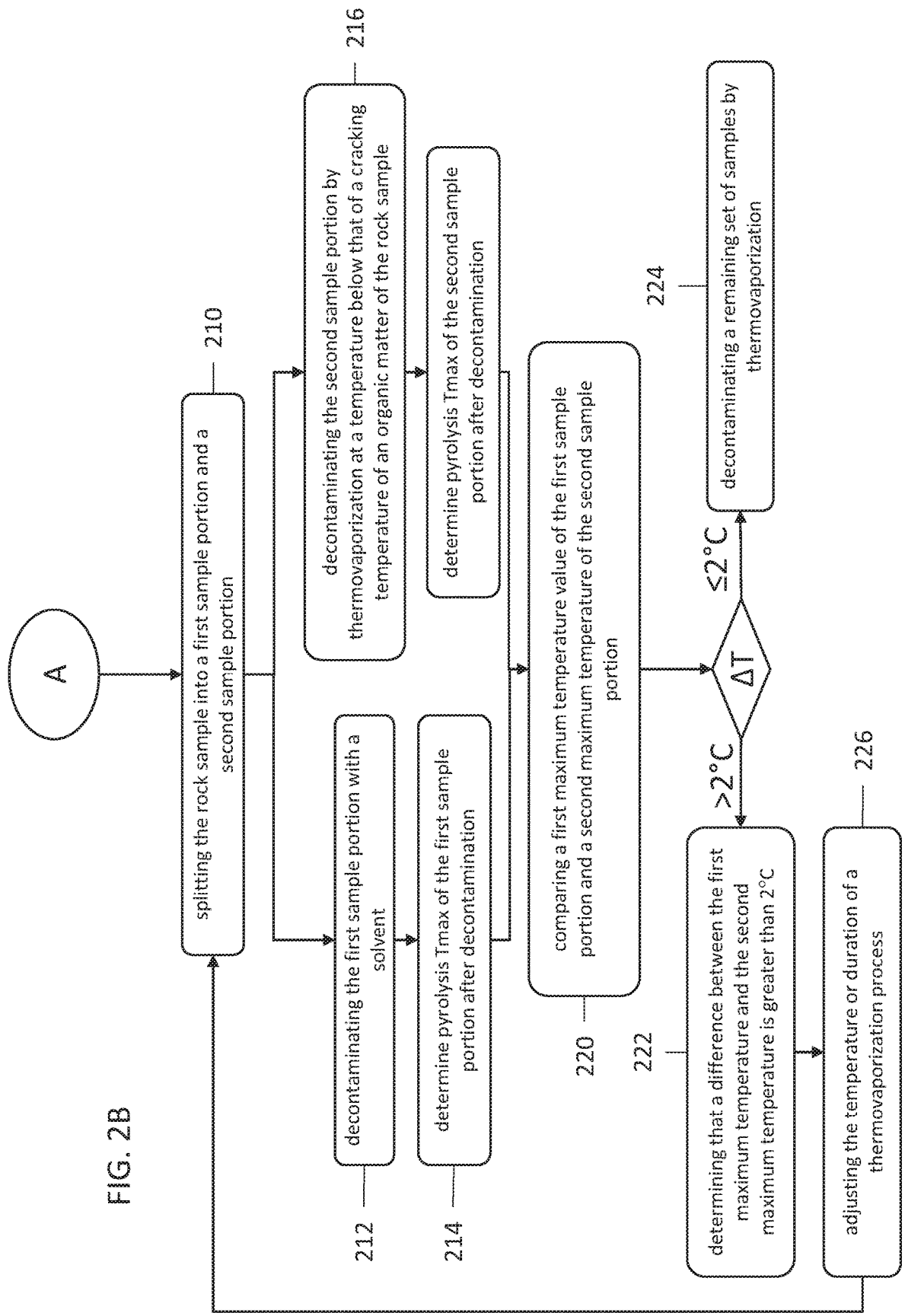

FIGS. 2A-2B shows a flowchart of an example method 200 that can be used to decontaminate a rock sample prior to pyrolysis. At 202, a rock sample of a geologic formation is received from a borehole formed in a geologic formation. At 204, the rock sample is prepared for pyrolysis testing. The sample preparation can include water-washing the rock sample, drying the rock sample, grinding the rock sample into smaller pieces, or any other preparation technique.

Next, a free hydrocarbon (residing in the pore space of the rock fragment and/or adsorbed on organic and mineral surfaces of the rock fragment) content (FHC) existing within the rock sample prior to pyrolysis and pyrolyzable hydrocarbon content (PHC) generated from pyrolysis of the rock sample are determined by routine programmed pyrolysis. Both quantities of FHC and PHC are determined in mg per gram sample. Signs of contamination can be determined based on the determined ratio of the FHC to the sum of FHC and PHC. For example, at 206, it is determined that there is no sign of contamination based on the ratio of the FHC to the sum of FHC and PHC of the rock sample. If such a determination is made, then decontamination is not necessary. However, at 208, it is determined that a rock sample obtained from a borehole is contaminated based on the ratio of the FHC to the sum of FHC and PHC of the rock sample. For example, if the ratio of the FHC to the sum of FHC and PHC of the rock sample is greater than approximately 0.5, then the rock sample can be considered contaminated. In some instances, the rock sample includes multiple rock sub-samples, or sample portions, each obtained from the same borehole. The multiple rock samples can be exposed to the same contamination during a drilling operation to drill the borehole. An organic contaminant can include diesel, oil-based drilling mud, or any other organic component added to the drilling fluid circulated through the borehole.

After it is determined that a rock sample is contaminated, at 210, the rock sample is split into a first sample portion and a second sample portion. At 212, the first sample portion is decontaminated with a solvent, such as an organic solvent. Decontaminating with the solvent can at least partially remove organic contaminants from the first sample. Several different solvents can be used depending upon the suspected contamination. For example, the solvent can include methanol, acetone, xylene, chloroform, dichloromethane, a mixture of the previously listed solvents, or any other solvent that is appropriate for dissolving organic contamination. After decontaminating the first sample portion with a solvent, the pyrolysis Tmax (the temperature, in Degrees Celsius, at which the yield of pyrolysis products is maximum) is determined at 214 for the first sample portion. This Tmax can be compared to the Tmax in the second sample portion after the second sample portion is decontaminated by thermovaporization rather than solvent extraction.

At 216, the second sample portion is decontaminated by thermovaporization for a duration of time at a thermovaporization temperature below that of a cracking temperature of organic matter carried within the rock sample. To do this, the thermovaporization temperature is elevated to a temperature greater than room temperature for a duration. For example, the thermovaporization temperature can be elevated to approximately 350° C. (within heating tolerances of the equipment) and the duration can be approximately 60 minutes (plus or minus five minutes). In another example, the thermovaporization temperature can be elevated to approximately 375° C. (within heating tolerances of the equipment) and the duration can be approximately 30 minutes (plus or minus five minutes). With both of the previously mentioned combinations of thermovaporization temperatures and durations, contaminants can be vaporized from a sample without cracking kerogen (solid organic matter) within the samples. If the temperature or duration is increased, then the kerogen within a sample can begin to crack and vaporize.

After the second sample portion has been decontaminated through thermovaporization, the Tmax of the second sample portion is determined by pyrolysis at 218. At 220, a first maximum temperature value of the first sample portion and a second maximum temperature of the second sample portion is compared. The maximum temperature of each portion corresponds to a maturity of the indigenous organic matter (kerogen) of each portion.

Next, at 222, a difference is determined between a first decontamination level of the first sample portion (decontaminated by the solvent) and a second decontamination level of the second sample portion (decontaminated by the thermovaporization). Based on the comparison, the effectiveness of the thermovaporization decontamination can be determined. For example, if a difference between a maximum temperature of the first sample portion by the solvent and a second maximum temperature of the second sample portion by the thermovaporization is less than 2° C., then the difference between a first decontamination level of the first sample portion by the solvent and a second decontamination level of the second sample portion by the thermovaporization is within acceptable limits. That is, the temperature and the duration of the thermovaporization is appropriate for removal of contaminants for the remaining samples. If that is the case, then, at 224, a remainder of the multiple rock samples is decontaminated by the thermovaporization in response to determining that the difference satisfies the decontamination level threshold.

In some instances, the remainder of the multiple rock samples can be prepared for decontamination by any of the methods previously described within this disclosure. The remainder of the multiple rock samples to be decontaminated by thermovaporization can be simultaneously decontaminated within the thermovaporization chamber 102. In some instances, the thermovaporization temperature of the remainder of the multiple samples is elevated to approximately 350° C. (within heating tolerances of the equipment) for a duration of approximately 60 minutes (for example, plus or minus five minutes). In some instances, the thermovaporization temperature can be elevated to approximately 375° C. (within heating tolerances of the equipment) and the duration can be approximately 30 minutes (for example, plus or minus five minutes).

In some instances, the determined difference between a Tmax of a first decontamination level of the first sample portion (decontaminated by the solvent) and a Tmax of a second decontamination level of the second sample portion (decontaminated by the thermovaporization) does not satisfy a decontamination level threshold (2° C.) based on the comparison. For example, at 222, a difference between a maximum temperature of the first sample portion by the solvent and a second maximum temperature of the second sample portion by the thermovaporization is greater than 2° C. With such a difference between a first decontamination level of the first sample portion by the solvent and a second decontamination level of the second sample portion by the thermovaporization being outside the acceptable limits, then, at 226, the temperature or duration of the thermovaporization process is adjusted. In such an instance, a second rock sample is taken from the multiple rock samples. The second rock sample, similarly to 204, can be split into a third sample portion and a fourth sample portion. Steps 210-220 are substantially repeated on the third and fourth sample portions. The steps can be repeated on other sample portions until the adjusted temperature and duration yield a determined difference between a first decontamination level of the first sample portion (decontaminated by the solvent) and a second decontamination level of the second sample portion (decontaminated by the thermovaporization) that satisfies a decontamination level threshold (less or equal to 2° C. difference in Tmax).

For example, similar to 212, the third sample portion can be decontaminated with a solvent that at least partially removes an organic contaminant from the third sample portion. Similar to 216, the fourth sample portion can be decontaminated by thermovaporization at an adjusted thermovaporization temperature value and an adjusted duration. The adjusted thermovaporization temperature can be lower than the initial thermovaporization temperature value or higher than the initial thermovaporization temperature value. The adjusted duration value of the thermovaporization process can be less than the initial duration value or greater than the initial duration value. In some implementations, if the thermovaporization temperature is adjusted, then the duration can be kept the same. In some implementations, if the duration is adjusted, then the thermovaporization temperature can be kept the same.

Similar to 220, a difference between a third decontamination level of the third sample portion (decontaminated by the solvent) and a fourth decontamination level of the fourth sample portion (decontaminated by the thermovaporization) temperature is determined. If the pre-determined threshold is reached, for example, the difference between the third maximum temperature and the fourth maximum temperature is within 2° C., then, similar to 222, the remaining set of samples can be decontaminated by thermovaporization by the adjusted temperature or duration of the thermovaporization process.

The remainder of the rock samples can be decontaminated by simultaneously thermovaporizing the remainder of the rock samples within a single thermovaporization chamber, such as the thermovaporization chamber 102. In one example, the adjusted thermovaporization temperature of the remainder of the samples is elevated to substantially 350° C. with a duration of thermovaporization of substantially 60 minutes.

Thus, particular implementations of the subject matter have been described. Other implementations are within the scope of the following claims.

What is claimed is:

1. A method of decontaminating a rock sample obtained from a borehole, the method comprising:
    thermovaporizing the rock sample to a thermovaporization temperature below that of a cracking temperature of organic matter carried within the rock sample, the thermovaporization temperature sufficient to at least partially decontaminate the rock sample;
    ceasing to thermovaporize the rock sample at the thermovaporization temperature;
    separating a portion of the rock sample from the rock sample prior to thermovaporization;
    decontaminating the portion with a solvent, wherein decontaminating at least partially removes an organic contaminant from the portion;
    determining that a difference between a first pyrolysis Tmax value of the portion decontaminated by the solvent and a second pyrolysis Tmax value of the portion of the decontaminated by the thermovaporization satisfies a decontamination level threshold; and
    decontaminating additional rock samples by the thermovaporization in response to determining that the difference satisfies the decontamination level threshold.

2. The method of claim 1, wherein the thermovaporization comprises heating up the rock sample while passing an inert carrier gas over the rock sample to at least partially decontaminate the rock sample.

3. The method of claim 1, wherein an initial thermovaporization temperature is elevated to substantially 375° C. and an initial duration of time is substantially 30 minutes.

4. The method of claim 1, wherein determining the difference between a first decontamination level portion of the rock sample decontaminated by the solvent and a second decontamination level of the rock sample by the thermovaporization comprises determining that a difference between the maximum temperature of the portion of the rock sample decontaminated by the solvent and the maximum temperature of the rock sample decontaminated by the thermovaporization is less than 2° C.

5. The method of claim 1, wherein decontaminating the rock sample comprises elevating an initial thermovaporization temperature to greater than 350° C. for an initial duration of time.

6. The method of claim 5, wherein the initial duration of time is substantially 60 minutes.

7. The method of claim 1, wherein the rock sample comprises a plurality of rock samples, wherein decontaminating the plurality of rock samples by the thermovaporization comprises simultaneously thermovaporizing the plurality of rock samples within a single thermovaporization chamber.

8. The method of claim 7, wherein the plurality of rock samples comprises seventy samples.

9. The method of claim 1, further comprising:
   adjusting an initial temperature of the thermovaporization or an initial duration of a thermovaporization process of a second rock sample, based on determining that the difference does not satisfy the decontamination level threshold.

10. The method of claim 9, wherein adjusting the duration of the thermovaporization process comprises shortening a duration to be less than the initial duration by an amount of time sufficient to prevent the organic matter within the rock sample from cracking.

* * * * *